United States Patent [19]

Dark

[11] Patent Number: 5,199,559
[45] Date of Patent: Apr. 6, 1993

[54] INTRAOCULAR LENS CASE
[75] Inventor: Stephen R. Dark, Riverside, Calif.
[73] Assignee: Ioptex Research, Inc., Irwindale, Calif.
[21] Appl. No.: 851,916
[22] Filed: Mar. 16, 1992
[51] Int. Cl.$^5$ .............................................. B65D 81/24
[52] U.S. Cl. ........................................ 206/5.1; 206/438; 623/6
[58] Field of Search ................ 206/5.1, 438; 356/246; 606/107; 623/6

[56] References Cited

U.S. PATENT DOCUMENTS

| | | | |
|---|---|---|---|
| 4,173,281 | 11/1979 | Trought | 206/5.1 |
| 4,205,747 | 6/1980 | Gilliam et al. | 206/5.1 |
| 4,269,307 | 5/1981 | LaHaye . | |
| 4,684,014 | 8/1987 | Davenport | 206/5.1 |
| 4,736,836 | 4/1988 | Alongi et al. | 206/5.1 |
| 4,817,789 | 4/1989 | Paul | 206/5.1 |

Primary Examiner—Bryon P. Gehman
Attorney, Agent, or Firm—Rosenman & Colin

[57] ABSTRACT

The present invention is directed to an intraocular lens (IOL) holder or case for holding, storing and transporting various types of intraocular lenses. The IOL holder or case is comprised of (a) a base having a recessed portion which contains a concave portion sized to hold and support an IOL of various sizes; (b) a cover for the base which has disposed therein a flexible insert; and (c) a system for locking the cover and the base in secure relationship to one another.

11 Claims, 4 Drawing Sheets

INTRAOCULAR LENS CASE

FIELD OF THE INVENTION

The present invention relates to intraocular lens (IOL) holders such as cases for holding, storing and transporting various types of IOLs, both those with and without loops or haptics.

BACKGROUND OF THE INVENTION

After fabrication, cleaning and inspection of intraocular lenses, the lenses are then typically placed in cases to be sterilized and ultimately shipped to customers. Most lens cases are designed and fabricated for a particular type of lens, such as a single-piece or multi-piece style of lenses.

The present invention comprises an IOL holder or case which, for the first time, has been designed to accommodate different styles of intraocular lenses. The primary advantages of the present invention are that: a) only one model of lens case has to be inventoried; b) incorrect packaging is eliminated; and c) costly insert changes of the injection mold are eliminated. The present invention is also functional as an IOL holder during the final phases of manufacturing. The holder or case has an opening on top and on bottom to permit sterilization degassing and further, to allow one to observe that the IOL secure.

SUMMARY OF THE INVENTION

The present invention is directed to an intraocular lens holder or case for holding, storing and transporting various types of intraocular lenses. It can, for example, accommodate circular IOLs, oval IOLs and IOLs with and without loops or haptics.

In one embodiment, the present invention contemplates an IOL case comprising a base having a recessed portion which contains a concave portion sized to hold and support an IOL with or without loops affixed to the lens or integral therewith; a cover for said base which has disposed therein a flexible insert; and a means for locking said cover and said base in secure relationship to one another.

In a further embodiment, the present invention comprises the IOL case described above with a bayonet type locking system, wherein the removable cover has at least one pair of retaining members and the base has at least one pair of retaining rails or locking members that permits a covering engagement with the retaining members.

In another embodiment, the present invention is directed to an IOL case as described in the first embodiment which additionally has a ramp locking system, i.e., wherein the removable cover member includes at least two locking members and the support member includes at least two apertures complementary to the locking members sized to receive the locking members by, for example, having an inner variable radial surface which permits a rotational interfacing with the locking members for locking engagement with the base.

In yet a further embodiment the present invention is directed to an IOL case wherein the base is in various shapes and sizes and can be integral with a case body.

In another embodiment the present invention relates to an IOL case wherein the flexible insert has an open, substantially circular central portion and four spokes radially extending therefrom and substantially equidistantly spaced from each other.

DETAILED DESCRIPTION OF THE INVENTION

The present invention relates to an IOL lens holder or case useful for holding, storing and transporting various styles of IOLs. More particularly, the present invention is directed to an IOL case having a base which stands alone or is integral with a case body, for holding the IOL. The base and case body can be injection molded from a suitable material such as, for example, polyolefin or KR01 K-resin polymers and is structured to have enough room to accommodate the label of the company manufacturing the IOL case and/or the IOL or other logos.

Figure 1:
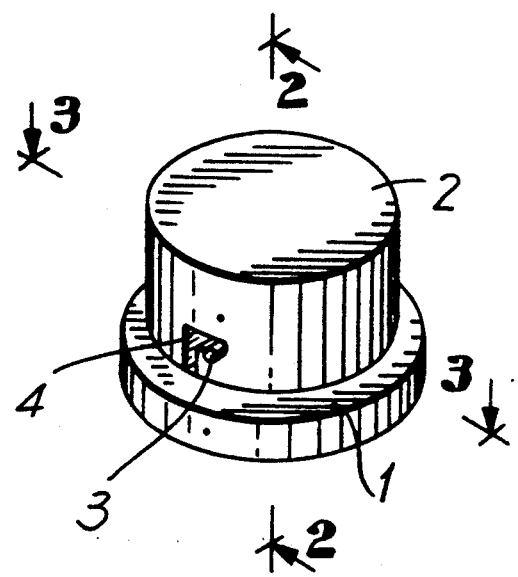
FIG. 1 is a perspective view of an embodiment of the present invention.

According to another embodiment, the present invention comprises an IOL case which comprises a base alone, an example of which is shown in FIG. 1. A cross-sectional view of the base is illustrated in FIG. 2; a planar view of the base is seen is FIG. 3.

Figure 2:
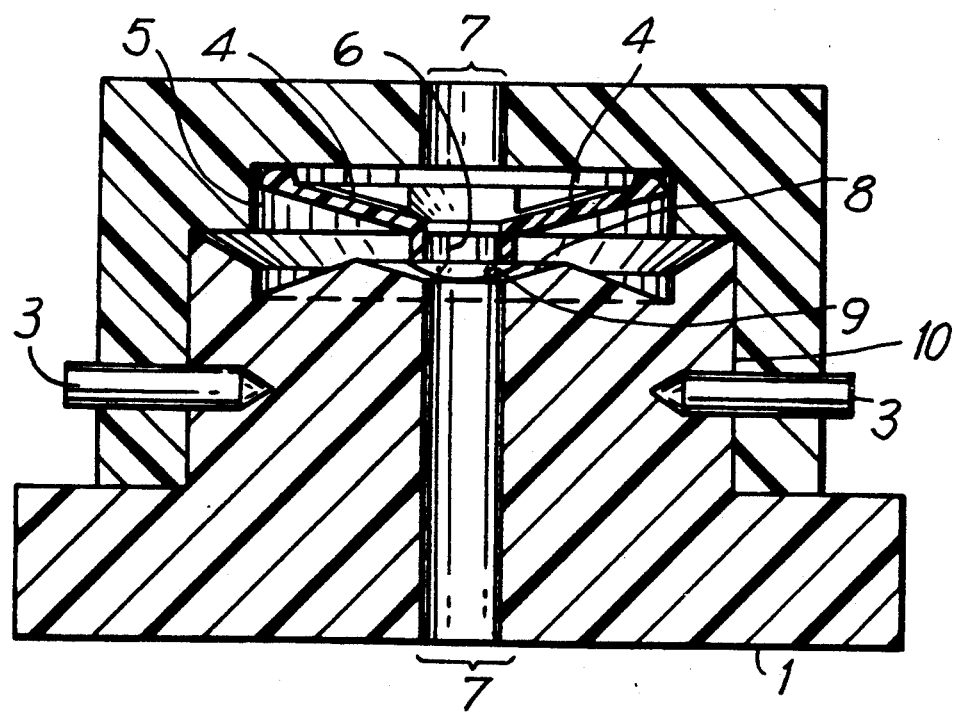
FIG. 2 is a cross-sectional side view of the same embodiment.
Figure 3:
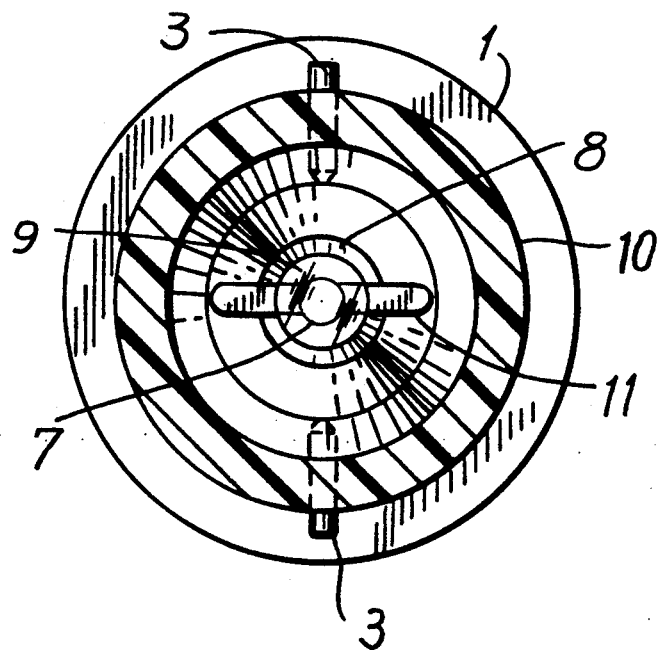
FIG. 3 is a planar view of the well of the embodiment shown in FIGS. 1 and 2.

The case shown in FIG. 1-3 utilizes the bayonet-style locking system. However, the present invention also contemplates utilization of a ramp-style locking system in place of the bayonet-style system.

The holder or case is comprised of three components: the cover, the base and the flexible insert. The base has a centrally located recessed concave portion for placement of the IOL. The cover has a recessed area into which the flexible insert is seated. The cover is placed over the base and rotated until the two pieces are tightly mated together. The flexible insert exerts a slight pressure onto the IOL when the cover is mated onto the base. The combination of the concave recessed portion of the base and the evenly dispersed pressure from the flexible insert on the surface of the IOL causes the IOL to center itself in the recessed area of the base.

Figure 4:
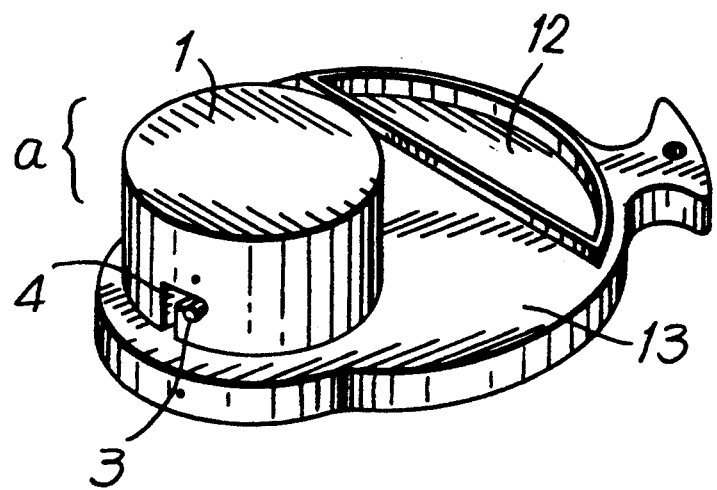
FIG. 4 is a perspective view of a further embodiment of the present invention.
Figure 5:
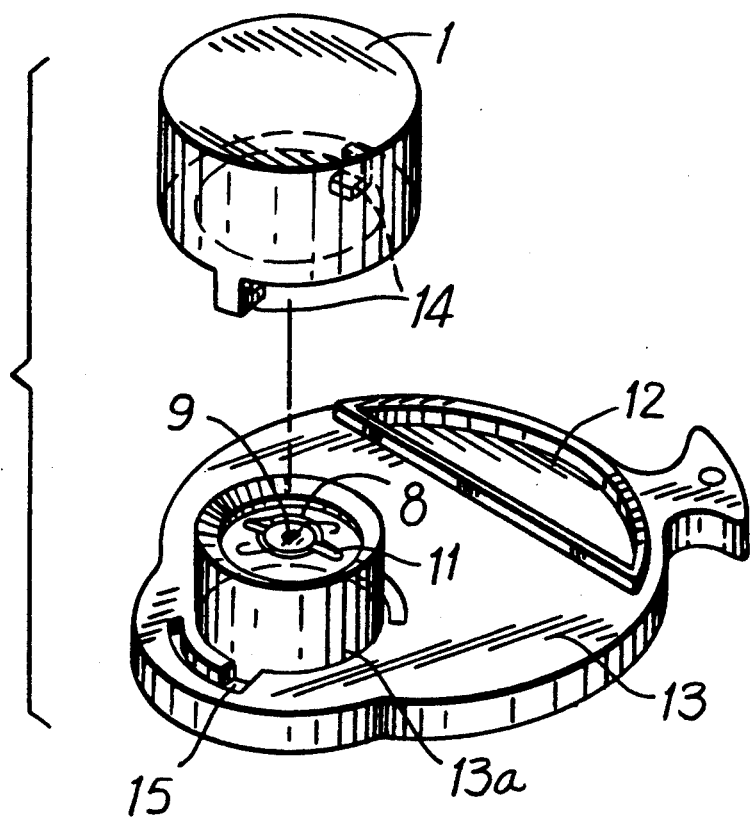
FIG. 5 is a perspective view of an embodiment of the present invention having a bayonet locking system.
Figure 6:
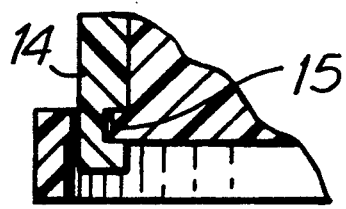
FIG. 6 is a cross-sectional view of the locking member of FIG. 5 fitted into the well case body support member.

The three components are further described as follows:

The cover can be fabricated from, for example, polyolefin or KR01 K-resin materials. The cover has a recessed area for placement of the flexible insert. The flexible insert, when fitted into the cover, will protrude from the bottom of the cover recess. In one embodiment, the cover has at least two recesses in the walls of the cover for utilization in a bayonet-type locking system. These recesses are oppositely disposed from one another in the cover, and can be, for example, of an inverted L-configuration, although any other formulations of the recesses which would allow an interlocking fit between the cover and the base are contemplated as well. This system can be used to mate the cover together with the base and comprises one type of IOL case contemplated by the present invention, as shown in FIG. 1, or the cover can be mated together with the base and case body as shown in FIG. 4. In another embodiment, the cover can have at least two locking members to be fitted into apertures located in the case body, i.e., surrounding the base, as shown in FIG. 5. In this embodiment, the base is connected to or integral with the case body. The fit of the locking member in the aperture is further illustrated in FIG. 6. When the cover is rotated in a form fitting and mating manner with the case body, it will lock into position and secure the IOL. The cover has a thru-hole which can be used to verify that the IOL is being held in place by the flexible insert.

Figure 7:
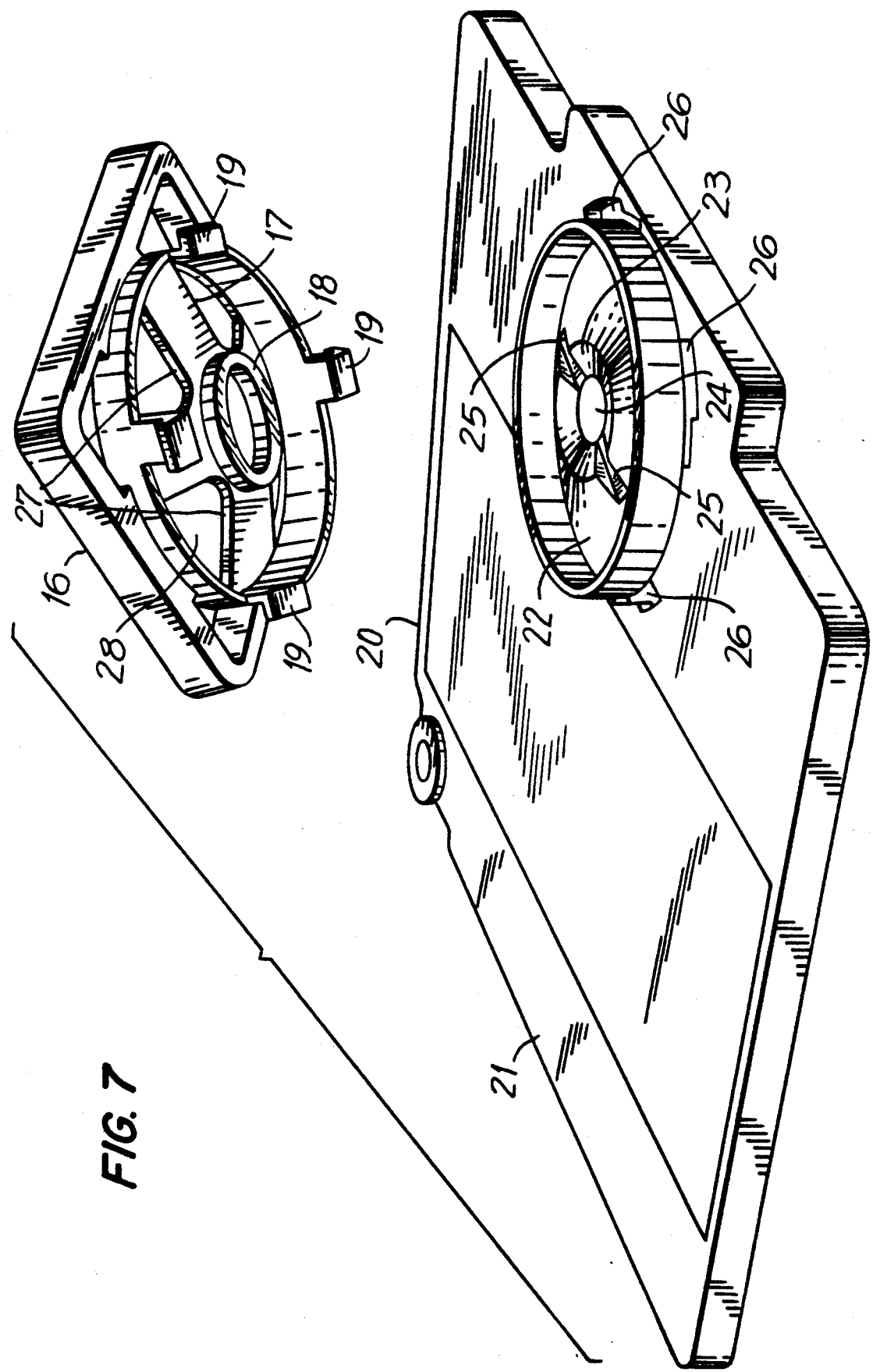
FIG. 7 is a perspective view of an embodiment of the present invention having four ramp style locking members.

The base can be made of a polymeric material, for example, polyolefin or KR01 K-resin. The base member alone or the base member connected to the case body, i.e., attached or molded to the case body which can be, for example, in a flat rectangular formulation as shown in FIG. 4, FIG. 5 and FIG. 7. The base member has a centrally located recessed concave area which can have at least one slot located on each side of a thru-hole in the center of the recessed area. These slots allow access of tweezers or forceps in order to achieve ease of lens removal. The concave recessed area has been centrally located in the base for optic placement of the intraocular lens. The thru-hole is located central to the well diameter to enable sterilization degassing and verification of the presence of the IOL in the case. In one embodiment, the base has at least two retaining rails for use in a bayonet-type locking system. In another embodiment the base or the case body connected to the base has apertures for use in a ramp locking system.

The flexible insert can be fabricated from any suitable flexible material. Polyolefins are an example of such suitable materials. This insert is a primary component of the sub-assembly of the IOL case. The insert is capable of inward and outward flexing movement, such as, for example, the flexible movement of a bellows. The flexible insert has a centrally located lip structure which can be circular (see, for example, FIG. 2, (5)). When the cover and the flexible insert sealed in the cover are placed over the base, the lip of the flexible insert contacts with the IOL sitting in the recessed concave area of the base. The flexible insert then flexes inward and the pressure is disbursed evenly around the periphery of the intraocular surface and of the lip. Various center thicknesses of optics are accommodated by the flexible insert. The lip of the flexible insert holds the IOL firmly in place when the cover is attached and secured to the base. Although thicker lenses cause the insert to flex slightly more than thinner lenses, all of these various IOLs can be held sufficiently by the lens case described herein. The height of the flexible insert and wall thickness are such that the insert places minimal pressure on high diopter lenses and maximum pressure on low diopter lenses in order to enable centration and effective securing of all styles of IOLs.

In a preferred embodiment, the flexible insert has a small dimple in order to enable a snap fit of the flexible insert into the cover. The flexible insert also has a hole and at least one, and preferably two, slots. These features give the insert flexibility and allow for optical access to the IOL. The flexible insert can have, for example, an open substantially central portion from which emanates the lip, and four spokes radially extending therefrom and substantially equidistantly spaced from each other.

Various embodiments of the present invention as shown in FIGS. 1-7 are described in further detail below. However, the present invention is not intended to be limited in any fashion by these particular embodiments.

FIG. 1 illustrates an embodiment of the invention, wherein the IOL case comprises the base member alone. In this particular embodiment, the base and cover utilize the bayonet-style locking system. The cover (2) is placed over the base (1) and mated to the base by attachment to a retaining rail or locking pin (3) which is fitted into a recess (4), which, as illustrated in FIG. 1 is of a substantially L-shaped configuration.

As shown in the cross-sectional view of the base in FIG. 2, the base (1) has two retaining rails (3) attached to the side walls (10) of the base to utilize in mating the cover (2) to the base. The flexible insert (4) fits in the recessed area (5) of the cover (2). The flexible insert (4) has a lip (6) which is capable of holding the IOL (9) in the centrally located recessed concave area (8) of the base. The cover and base each have a thru-hole (7) which allows one to verify that the IOL is being held centrally in the case.

The planar view of this embodiment of the IOL case in FIG. 3 shows the base (1) in detail. It illustrates that the centrally located recessed concave area (8) has a thru-hole (7) in the center and two slots (11), one on each side of the thru-hole, and disposed opposite each other. The retaining rail (3) is embedded within the side wall (10) of the base (1).

In another embodiment in FIG. 4, the present invention contemplates a case (a) wherein the base is integral with the case body (13). The case body has a space 12) for the logo or trademark of the company manufacturing the case. The base is the same as that in FIGS. 1-3, except that in this embodiment, the base is attached to or integral with the case body. The cover (1) is mated to the base by the retaining rail (3) locking in the inverted-L configuration recess (4).

FIG. 5 illustrates another version of the IOL case which comprises a base integral with the case body wherein the cover (1) is attached to the base (13a) by a ramp locking system. The cover (1) has two locking members (14). There are two apertures (15) for the locking member in the case body (113) surrounding the attached base (13a). The fit of the locking member (14) to the aperture (15) is further detailed in FIG. 6. Although the locking mechanism differs from that shown in FIGS. 1-4, the other basic features of the cover (1) and base (13a) are the same. For example, the cover has a flexible insert (which is not shown) and a thru-hole. The base has a centrally located recessed concave area (8) for an IOL (9), two slots (11) and a thru-hole (not shown).

FIG. 7 illustrates a further embodiment of the present invention. This figure shows a base (22) integral with case body (20), cover (16) and flexible insert (17) attached to a cover (20) wherein the cover (16) has four locking members (19). The case body (20) has a space (21) for the manufacturer's trademark or logo. Surrounding the base are four apertures (26) for holding the locking members (19) of the cover (16). The base has a centrally located recessed concave area (23), a thru-hole (24) and two slots (25). The cover (16) has a recessed area (28). The flexible insert (17) is inserted in the recessed area (28) and has four spokes (27) and a lip (18).

The case shown in FIG. 7 utilizes a ramp-style locking system.

We claim:

1. An intraocular lens (IOL) holder which comprises:
   (a) a base having a recessed portion which contains a concave portion sized to hold and support and IOL with or without loops affixed thereto or integral therewith;
   (b) a cover for the base which has disposed therein a flexible insert wherein the flexible insert has an open, substantially circular central portion and spokes radially extending therefrom and substantially equidistantly spaced from each other; and
   (c) means for locking said cover and said holder base in secure relationship to one another.

2. A holder according to claim 1 wherein the flexible insert is capable of contacting with an IOL when the cover is placed on the base, and further wherein said flexible insert holds the IOL in place when the cover is attached and secured to the base.

3. A holder according to claim 1 or 2 wherein the locking means comprises at least two retaining rails disposed at opposite sides of the base of the holder and extending outwardly from said base, and at least two recesses oppositely disposed from one another in said cover, said recesses being of a substantially inverted L-configuration, that permit a sliding engagement with the retaining rails.

4. A holder according to claim 1 or 2 wherein the locking means comprises at least two locking members extending downwardly from said cover and being spaced equivalently from one another and a corresponding number of complementary apertures in said case body sized to receive said locking members.

5. An intraocular lens (IOL) holder which comprises:
   (a) a base having a recessed portion which contains a concave portion sized to hold and support an IOL with or without loops affixed thereto or integral therewith, and further, wherein said base is integral with a case body;
   (b) a cover for the base which has disposed therein a flexible insert wherein the flexible insert has an open, substantially circular central portion and spokes radially extending therefrom and substantially equidistantly spaced from each other; and
   (c) means for locking said cover and said holder base in secure relationship to one another.

6. A holder according to claim 5 wherein said case body has a space for a logo or trademark.

7. A holder according to claim 6 wherein the flexible insert is capable of contacting with an IOL when the cover is placed on the base, and further wherein said flexible insert holds the IOL in place when the cover is attached and secured to the base.

8. A holder according to claim 5 wherein the flexible insert is capable of contacting with an IOL when the cover is placed on the base, and further wherein said flexible insert holds the IOL in place when the cover is attached and secured to the base.

9. A holder according to claims 8 or 7 wherein the locking means comprises at least two retaining rails disposed at opposite sides of the base of the holding member and extending outwardly from said base, and at least two recesses oppositely disposed from one another in said cover, said recesses being of a substantially inverted L-configuration, that permit a sliding engagement with the retaining rails.

10. A holder according to claims 8 or 7 wherein the locking means comprises at least two locking members extending downwardly from said cover and being spaced equivalently from one another and a corresponding number of complementary apertures in said case body sized to receive said locking members.

11. A holder according to claim 1 or 5 wherein said base and said cover each have a thru-hole.

* * * * *